United States Patent [19]

Groman et al.

[11] 4,397,779
[45] Aug. 9, 1983

[54] PREPARATION OF XANTHINE TRACERS

[75] Inventors: Ernest V. Groman, Somerville; Michael D. Cabelli, Waltham, both of Mass.

[73] Assignee: Baxter Travenol Laboratories, Inc., Deerfield, Ill.

[21] Appl. No.: 267,952

[22] Filed: May 28, 1981

Related U.S. Application Data

[62] Division of Ser. No. 932,146, Aug. 9, 1978, Pat. No. 4,297,494.

[51] Int. Cl.³ .......................................... C07D 473/04
[52] U.S. Cl. ............................ 260/112.5 R; 544/268; 544/269; 544/267; 544/270
[58] Field of Search ............... 544/267, 268, 269, 270; 260/112.5 R

[56] References Cited

U.S. PATENT DOCUMENTS

| 4,247,453 | 1/1981 | Ali | 260/112.5 R |
| 4,297,263 | 10/1981 | Buckler et al. | 260/112.5 R |
| 4,297,494 | 10/1981 | Groman et al. | 544/267 |

Primary Examiner—Nicholas S. Rizzo

Attorney, Agent, or Firm—Max D. Hensley; Lawrence W. Flynn; Paul C. Flattery

[57] ABSTRACT

Compounds useful as tracers in the radioimmunoassay of xanthine derivatives such as theophylline and pharmacologically related drugs:

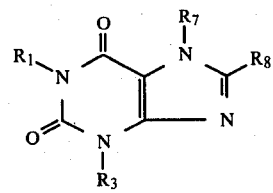

wherein at least one $R_1$, $R_3$, $R_7$ or $R_8$ is a radioiodinated radical and wherein, if not substituted by a radioiodinated radical, the remaining $R_1$, $R_3$, $R_7$ or $R_8$ groups are otherwise identical to the substituents at these positions in the xanthine derivative to be assayed. Ordinarily, $R_1$ is hydrogen, acetate or methyl; $R_3$ is methyl; $R_7$ is hydrogen, acetate or methyl; and $R_8$ is hydrogen. The tracers are made by linking radioiodinatable or preradioiodinated radicals to the xanthine derivative which is to be assayed. The tracers may be employed in known radioimmunoassay techniques.

8 Claims, No Drawings

PREPARATION OF XANTHINE TRACERS

This is a division of application No. 932,146 filed Aug. 9, 1978, now U.S. Pat. No. 4,297,494.

This invention broadly relates to the radioimmunoassay of xanthine derivatives. In particular, this invention relates to the radiolabeled xanthine derivatives employed in such assays, their methods of preparation and use as well as certain novel intermediates formed in their manufacture.

BACKGROUND OF THE INVENTION

A number of xanthine derivatives exhibit biological activity. These derivatives are generally 1, 3 or 7 lower alkyl-substituted, and their activity varies depending upon which of these positions of the xanthine nucleus are alkylated. For example, theophylline, theobromine and caffeine differ from one another solely by the location of methyl groups at these three sites.

Theophylline is a particularly important biologically active xanthine derivative (1,3-dimethylxanthine). Theophylline is a bronchodilator which can be useful in the treatment of asthma. The importance of monitoring theophylline levels is illustrated by the finding of widely varying serum theophylline concentrations in patients receiving identical doses. Since theophylline is metabolized in the liver, factors which affect the liver may affect theophylline metabolism resulting in modified serum half-lifes. Factors such as cigarette smoking, chronic theophylline therapy, alcoholism, barbiturates, allopurinol, and impaired hepatic or renal function may lead to toxic or inadequate dosing. Differences in serum levels between individuals may arise from the drug form used (tablet, suppository, elixir), site administration (oral, rectal), and rate and quantity of theophylline absorbed. This is in part a result of the low solubility of theophylline in the gastrointestinal environment.

Titering of serum theophylline levels is particularly important in infant care because premature infants have a greater sensitivity to adverse side effects of high theophylline levels and because the serum half-life of theophylline in premature infants is longer and more variable than in adults or older children.

Gas liquid chromatography, high pressure liquid chromatography and spectrophotometry have been used to determine concentrations of theophylline and other xanthine derivatives. These techniques tend to be more labor intensive and less rapid for multisample batch sizes than radioimmunoassay methods.

Radioimmunoassay requires smaller sample sizes than the above methods. This is an advantage for titering theophylline levels in premature infants. However, prior radioimmunoassay methods for theophylline have employed tritiated theophylline as tracer. This has necessitated the use of scintillation counting of tritium, a considerably less convenient technique than gamma counting of iodine isotopes. Tritium labeled tracers also have a lower specific activity than iodinated tracers, thus limiting the sensitivity of the radioimmunoassay. Finally, tritium may have a tendency to exchange with hydrogen ions in solution depending upon the substitution site.

It is therefore an object of this invention to provide new xanthine derivatives which are useful in the preparation of tracers for the radioimmunoassay of theophylline and related compounds.

It is a further object of this invention to provide radioiodinated xanthine derivatives useful as tracers in the radioimmunoassay of theophylline and related compounds.

These and other objects of this invention will be apparent to those skilled in the art from a consideration of this specification taken in its entirety.

SUMMARY OF THE INVENTION

The above objectives are accomplished by providing tracers having the following structural formula:

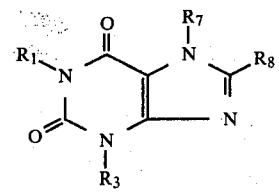

Wherein at least one $R_1$, $R_3$, $R_7$ or $R_8$ is a radioiodinated radical and wherein, if not substituted by a radioiodinated radical, the remaining $R_1$, $R_3$, $R_7$ or $R_8$ groups are otherwise identical to the substituents at these positions in the xanthine derivative to be assayed. Ordinarily, if not substituted with a radioiodinated radical, $R_1$ is hydrogen, acetate or methyl; $R_3$ is methyl; $R_7$ is hydrogen, acetate or methyl; and $R_8$ is hydrogen.

Any one or more of $R_1$, $R_3$, $R_7$ or $R_8$ may be selected as the point of substitution of the radioiodinated radical, depending upon the xanthine derivative to be assayed. As a general rule the radioiodinated radical should be substituted at a point on the xanthine ring which is as distant as possible from the portions of the ring which distinguish the xanthine derivatives to be detected and discriminated. Thus it is unusual for more than two of the above four positions to be substituted with radioiodinated radicals.

The structure of the radioiodinated radical is not critical; its purpose is merely to link a radioisotope of iodine such as $^{125}I$ or $^{131}I$ to the xanthine moiety. However, it should be neither so large as to adversely affect binding of the tracer to antibody nor capable of reacting adversely with radioimmunoassay reagents or samples.

The radical will generally fall within the class of unsaturated rings, usually heterocycles but also hydroxylsubstituted, unsaturated cyclic hydrocarbons, and aliphatic radicals. The aliphatic radicals may be branched or normal, saturated or unsaturated. Ordinarily, the aliphatic radicals will be normal hydrocarbons containing from 1 to about 10 carbon atoms and having at least one double bond. Xanthine derivatives having haloalkyl substituents, including iodoalkyl groups, are well known. Such derivatives may be employed as tracers in this invention by following the prior art syntheses but with the replacement of radioiodine for nonisotopic iodine. While radioiodinated aliphatic radicals are useful it is preferred to employ radioiodinated rings, particularly unsaturated heterocycles. Radioiodinated alkenyls are preferred over radioiodinated alkyls.

Ordinarily the radioiodinated radical will be the group $L(Z)_n$, wherein L is a linking group, Z is a radioiodinated ring and n ranges from 1 to about 10. However, it is also contemplated that tracers of this invention will contain no linking group but instead a direct bond between the radioiodinated ring and the xanthine moiety. Under certain circumstances both the linking group and the ring will be radioiodinated. The total molecular weight of the $L(Z)_n$ moiety ordinarily will not exceed 2000 and is generally less than 1000.

The linking group is ordinarily a product of the process used for binding a radioiodinatable or preradioiodinated ring to the xanthine moiety. It is preferably a hydrocarbon, or several hydrocarbon radicals joined by ester, ether, or amide groups. The hydrocarbon groups may in turn be substituted with halo, hydroxy, keto, carboxy, alkoxy, alkoxycarbonyl, alkylamio or amino groups. Representative linking groups are the cyclic, normal or branched alkylenes or alkenylenes, such as alkylenes and alkenylenes substituted with hydroxy, keto, carboxy or amino groups; esters; ethers; carboxyl or phosphoryl esters; amines and amides.

The rings employed in the radioiodinated radicals are generally phenol, imidazole or indole radicals having the following structures.

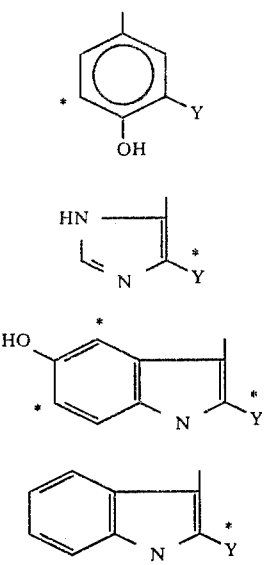

Wherein Y is hydrogen, halo or lower alkyl up to about 7 carbon atoms. These radicals may then be radiolabeled, preferably radioiodinated with one radioiodine atom at the positions of labeling indicated with an asterisk. The radicals may be radioiodinated at the Y position where Y is hydrogen prior to radioiodination. Other rings such as pyrrole, furan or thiophene may also be employed. The use of these rings as opposed to an aliphatic or branched chain radioiodinated radical is favored because of the generally greater stability of iodination. However, this advantage may in some cases be offset by the bulkiness of the ring and its consequent effect on antibody binding.

Also included within the scope of this invention are xanthine derivatives which are capable of radioiodination in the synthesis of the novel tracers herein. When a ring or substituent is said to be radioiodinatable or capable of radioiodination it is meant that iodine may be added to or otherwise incorporated into that ring or substituent without iodination of the xanthine ring, such as by the radioiodination methods disclosed herein. These tracer precursors are generally conjugates of xanthine and at least one of the radioiodinatable rings described above in which the rings are linked to at least one of the xanthine 1, 3, 7 or 8 positions, although alkanols and alkenyls, particularly polyalkenyls, may be conjugated to the xanthine nucleus at one or more of the 1, 3, 7 or 8 positions.

The tracers of this invention have broad use in any radioimmunoassay technique wherein a sample is contacted with a constant amount of tracer and an antibody which will selectively bind the sample xanthine and the tracer, followed by measuring the degree of binding of the tracer to the antibody. The tracers of this invention may be used with any of the various techniques for radioimmunoassay which employ a tracer for the substance tested, including primarily the competitive and saturation methods. The compounds to which such radioimmunoassays are directed do not need to be drugs but can be biologically inactive intermediates used in the production of the drugs or found as in vivo metabolites. Caffeine in biological fluids or in consumer goods may also be measured by such methods.

A novel method of synthesizing these tracers comprises forming an 8-alkanoic acid of xanthine by condensing a diamino pyrimidinedione with a cyclic anhydride, followed by formation of an amide bond between the xanthinealkanoic acid and an amino-substituted radioiodinatable or radioiodinated ring using alkyl chloroformate activation of the alkanoic acid. Alternatively, an 8-aminoalkyl xanthine derivatives may be reacted in the same fashion with an activated carboxyl-substituted radioiodinatable or radioiodinated ring. Here, however, unless a protective group is present on the 7 position nitrogen it is likely that both 7 and 8 substitution will occur, thereby necessitating conventional isolation procedures if a monosubstituted tracer is desired.

The particular amino-substituted rings are ordinarily selected from the aminoalkyl, aminoalkanol or aminoalkanoic acid derivatives of radioiodinatable rings such as indole, phenol or imidazole. Suitable amino derivatives are tyrosine, histidine, histamine, 4-hydroxyphenylglycine or tyrosinol. However, amino-terminated polypeptide radicals containing at least one of the aforesaid radioiodinatable rings may also be employed, although polypeptides containing more than about 10 amino acid residues are not desirable. Polypeptides above this size may adversely affect antibody binding, and they may be unstable in storage. The polypeptide substituents used in the tracers of this invention should exhibit neither antigenic nor enzymatic activity.

In the final step of this method the radioiodinatable ring is radioiodinated with $^{125}I$ or $^{131}I$ by known techniques such as those described infra. This step will of course be redundant if the ring has been radioiodinated prior to condensation with the xanthine ring.

Certain radioiodinatable xanthine derivatives within the scope of this invention are novel. These derivatives comprise compounds having the formula:

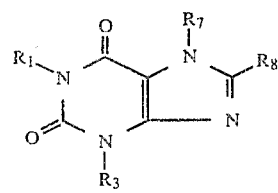

wherein
(a) $R_1$ is an imidazole, pyrrole, thiophene, indole or polyunsaturated alkenyl radical;
(b) $R_3$ is a nonenzymatic radioiodinatable radical, in particular an unsaturated heterocyclic radical or a hydroxy-substituted, unsaturated cyclic hydrocarbon radical;
(c) $R_7$ is a pyrrole, furan, thiophene, polyunsaturated alkenyl, imidazole or indole radical, with the proviso that
(1) the imidazole radical has the structure —$L(X)_n$ wherein
L is a linking group containing at least one ester, ether, amide or amino bond, X is imidazole and n ranges from 1 to about 10; and
(2) the indole radical has the structure:

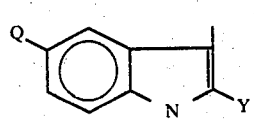

wherein Q is hydrogen or hydroxyl and Y is hydrogen, halo or lower alkyl up to about 7 carbon atoms; and
(d) $R_8$ is a pyrrole, furan or imidazole radical wherein the imidazole radical is set forth in part (c)(1); with the proviso that no more than two of $R_1$, $R_3$, $R_7$ or $R_8$ are the above radicals and that if $R_1$, $R_3$, $R_7$ or $R_8$ are not one of the above radicals then $R_1$ is hydrogen, acetate or methyl; $R_3$ is methyl; $R_7$ is hydrogen, acetate or methyl; and $R_8$ is hydrogen.

DESCRIPTION OF THE PREFERRED EMBODIMENTS

The following is a tabulation of the predominant, pharmacologically active xanthine derivatives to which the radioimmunoassays of the invention may be directed using the novel tracers of this invention.

Theophylline

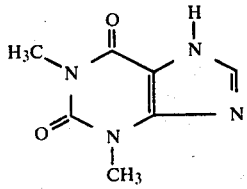

7-Theophyllineacetic Acid

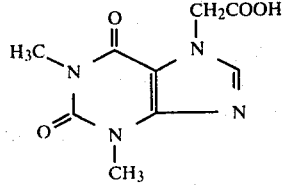

1-Theobromineacetic Acid

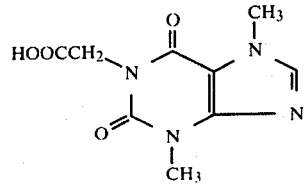

Caffeine

Theobromine

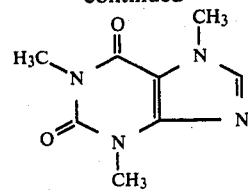

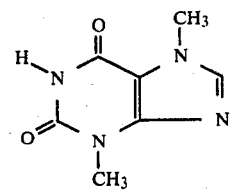

Substituents $R_1$, $R_3$, $R_7$ and $R_8$, when not representing a radioiodinated radical, are relevant only insofar as they represent the same substituents found in the xanthine to which the assay is directed. The xanthine tracer should vary as little as possible from the target xanthine so as to successfully mimic the binding of target to its antibody. Thus, for example, a tracer suitable for use in the radioimmunoassay of theophylline will have $R_1$ and $R_3$ substituted with methyl, $R_7$ with hydrogen and $R_8$ with a radioiodinated radical. Alternatively, $R_3$ may be substituted with a radioiodinated radical in place of methyl.

Theobromine tracers will also be $R_3$ or $R_8$, or both $R_3$ and $R_8$ substituted. Here, however, $R_1$ will be hydrogen rather than methyl because this feature distinguishes theobromine from theophylline.

Caffeine tracers should only be 8-substituted because the presence of methyl at the $R_7$ position distinguishes caffeine from theophylline. Of course, if theophylline is not expected to be present in the sample or can be removed then 1,3-dimethylxanthine radioiodinated at the $R_7$ position may be employed. Generally, tracers having the radioiodinated radical at the $R_7$ position are least desired while $R_3$ and, particularly, $R_8$ are preferred. Cross reactivity is not a bar to use of a tracer in an assay where the interference from the cross reactive substance may be discounted at the desired level of accuracy, where the substance ordinarily will be present in insignificant or known amounts, or where it may be removed by adsorption and the like.

The structure of the relevant portions of the xanthine derivative to be assayed generally will be known at the time the tracer is prepared, as will the presence or absence of potentially interfering, related xanthine derivatives, so the skilled artisan will be able to readily select the appropriate site or sites for substitution of radioiodinated radicals. In fact, the starting material for synthesis of the tracers may be the xanthine derivative itself. Thus in this case it would not even be necessary to know the structure of the xanthine for which one is testing.

The radioiodinated radical may be aliphatic, cyclic or both combined. Where the radical is aliphatic it will contain from 1 to about 10 carbon atoms. It is preferred to employ from 3 to 6 carbon atoms in a normal rather than branched configuration with the radioiodine substituted as distant as possible from the xanthine nucleus. It is also preferred that the aliphatic radical be alkenyl. In such a case it is most desirable that radioiodine be substituted at or α to a double bond. The aliphatic radicals are also preferably substituted with groups which will increase their solubility, particularly hydroxyl, amino, carboxyl and keto. However, other substituents such as alkoxy, halo, alkoxycarbonyl or alkylamino groups may also be present.

Also within the scope of this invention are tracers wherein the 8 position of the xanthine ring is directly substituted with an atom or radioiodide. 8-iodotheophylline, for example, is well-known and may be synthesized using $^{125}$I to yield tracers suitable for use according to this invention.

Ordinarily the radioiodinated radicals of this invention will be radioiodinated rings which are bonded to the xanthine nucleus directly or, preferably, through a linking group. The rings are preferably unsaturated carbocycles having a ring hydroxyl substituent or unsaturated heterocycles. Exemplary of the latter are imidazole, indole, pyrrole, furan and thiophene, with imidazole being preferred. Phenol is an example of the former. 6-hydroxyindole is a hybrid of both types of rings. These rings should be bonded through the ring carbon atoms to the xanthine nucleus or the linking group at a position as distant as possible from the ring hydroxyl group or non-carbon atoms.

Where a linking group is employed the radioiodinated radical will have the structure L(Z)$_n$ as described generally above. The number of Z rings, n, is usually one or two, with one being preferred, but if a high tracer specific activity is desired then n may be greater than 2.

L is a bond or is generally selected from one of the radicals:

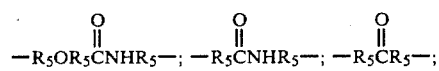

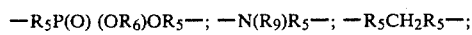

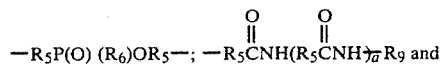

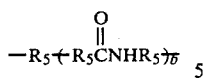

wherein
(i) R$_5$ is a bond; a substituted or unsubstituted hydrocarbon, ordinarily a cyclic, normal or branched alkylene or alkenylene; or such alkylene or alkenylene substituted with halo, hydroxy, keto, carboxy, alkoxy, alkoxycarbonyl, amino or alkylamino groups;
(ii) R$_6$ is alkyl of from 1 to about 6 carbon atoms;
(iii) R$_9$ is hydrogen or a substituted or unsubstituted hydrocarbon, ordinarily a cyclic normal or branched alkylene or alkenylene; or such alkylene or alkenylene substituted with halo, hydroxy, keto, carboxy, alkoxy, alkoxycarbonyl, amino or alkylamino groups;
(iv) a ranges from 1 to about 10; and
(v) b is 2 or 3.

The structures

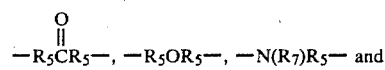

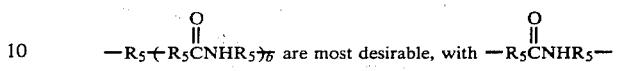

being preferred.

R$_5$ and R$_9$ may represent the same or different alkylene or alkenylene groups. These groups should generally contain from 1 to about 10 carbon atoms. Fully saturated, straight or branched chain hydrocarbons of from 1 to about 5 carbon atoms are preferred. They ordinarily will contain no more than two halo, hydroxy, keto, carboxy, alkoxycarbonyl, amino or alkylamino substituents. The keto, hydroxy, carboxy or amino substituents are preferred. Halogen substituents may include bromine, chlorine or nonradioactive iodine. The alkoxy, alkylamino or alkoxycarbonyl groups will generally contain normal hydrocarbons of from 1 to about 3 carbon atoms.

Representative cyclic R$_5$ or R$_9$ groups are cyclohexyl, cyclopentyl, and phenyl, but here as in aliphatic hydrocarbons it is desirable to substitute the carbon atoms with radicals such as keto, hydroxy, carboxy or amino to increase the solubility of the tracers or their precursors. Other substituents which may be employed with cyclic R$_5$ or R$_9$ radicals include halogen such as bromine, chlorine or nonradioactive iodine, and alkoxy, alkylamino or alkoxycarbonyl where the alkyl is a normal or branched hydrocarbon of from 1 to about 3 carbon atoms.

Examples of aliphatic R$_5$ are ethylene, methylene, 2-hydroxy propylene, 3-hydroxypropylene, 3-ethyl-2-pentynylene, isopropylene, butylene, isobutylene, 3-aminoisobutylene, 3-dimethylaminoisobutylene, 2-hydroxyisobutylene, heptylene, 2-aminoheptylene, hexylene, 2-ethylheptylene, 2-hydroxyheptylene, 1-carboxyethylene, 3-carboxymethyl hexylene, 3-methoxyheptylene and 1-hydroxymethylethylene. It is most preferred that R$_5$ be an unsubstituted, normal alkylene of 3 to 5 carbon atoms, for example butylene. Suitable R$_9$ groups include all of the foregoing for R$_5$ except that the groups will be monovalent, for example ethyl or isobutyl.

In the novel radioiodinatable xanthine derivatives or tracer precursors described above, R$_1$ is preferably an imidazole radical. R$_3$ is preferably an unsaturated heterocyclic radical such as imidazole, although a phenol radical is also satisfactory. If R$_3$ is a polypeptide containing such a radical then the polypeptide should be neither antigenic nor enzymatic.

R$_7$ is preferably an imidazole-containing radical as well, although in the case of this position the imidazole ring should be linked to the xanthine nucleus by a linking group which includes an ester, ether, amide or amino bond.

Suitable linking groups are $$-R_5OR_5CNHR_5-; \quad -R_5CNHR_5-; \quad -R_5COR_5-; \quad -R_5OR_5-;$$

-continued

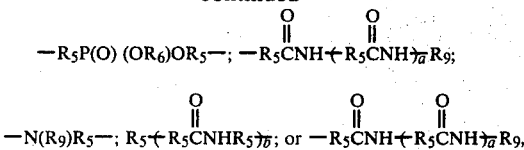

wherein $R_5$, a, b and $R_9$ are defined above. The group

is preferred.

$R_8$ is preferably an imidazole radical as defined above.

Unless otherwise specified, the radioiodinatable rings set forth above may be directly bonded to the xanthine nucleus or linked by way of a linking group L which may be solely a carbon chain without any intervening ester, ether, amide or amino bond as is the case with $R_7$. The polyunsaturated alkenyl substituents found at $R_1$, $R_3$ or $R_7$ are preferably conjugated dienes having from 5 to 10 carbon atoms, most preferably pentadienyl.

The following table includes representative tracers within the scope of this invention. The tracer precursor compounds will be identical to those in this table except that hydrogen is present instead of $^{125}I$ or $^{131}I$. The first compound is the preferred tracer.

TABLE

Xanthine Tracers

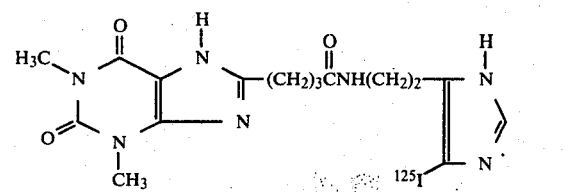 1.

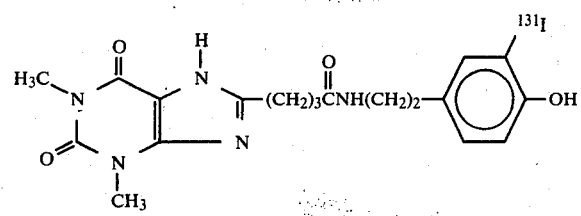 2.

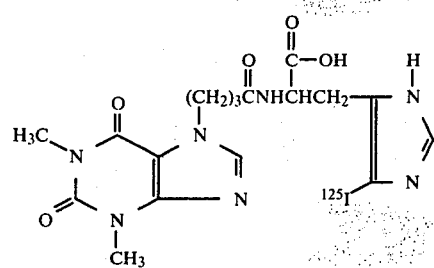 3.

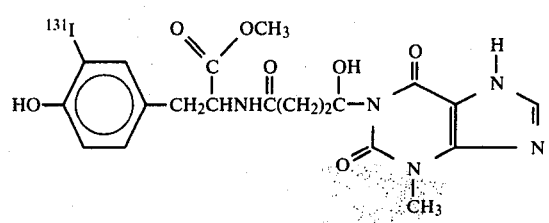 4.

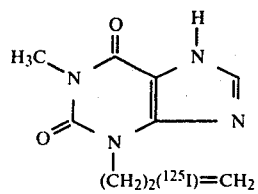 5.

TABLE-continued
Xanthine Tracers
6. 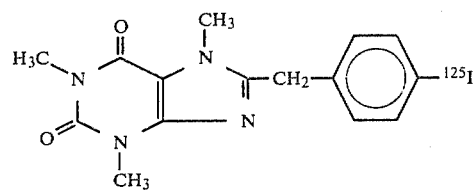
7. 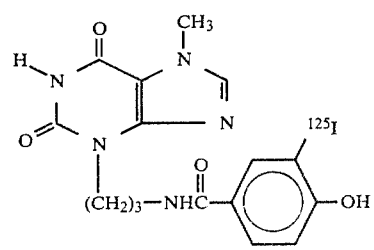
8. 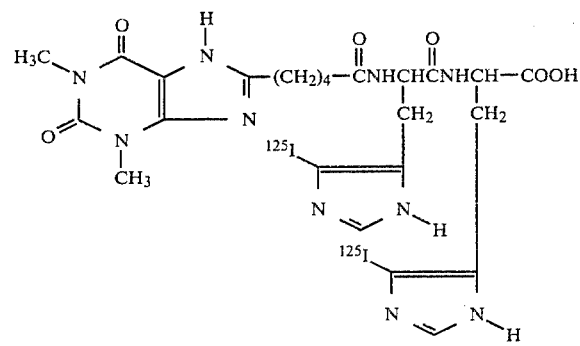
9. 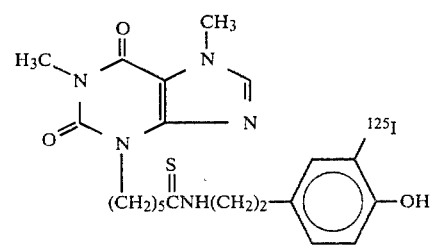
10. 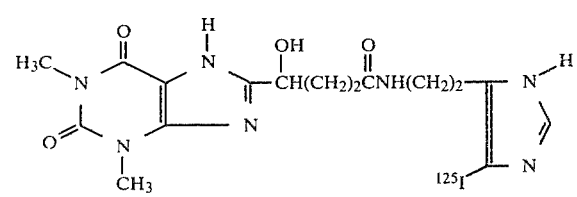
11. 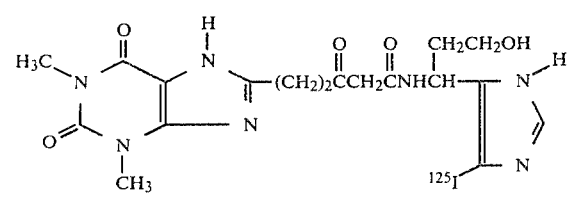

TABLE-continued
Xanthine Tracers
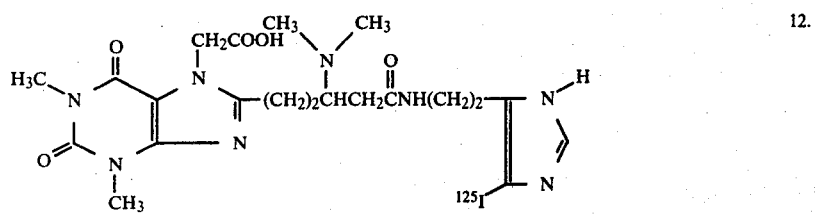 12.
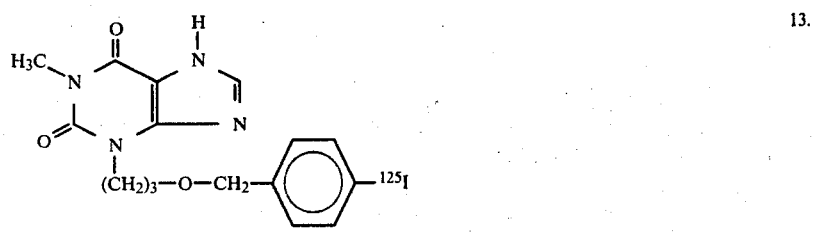 13.
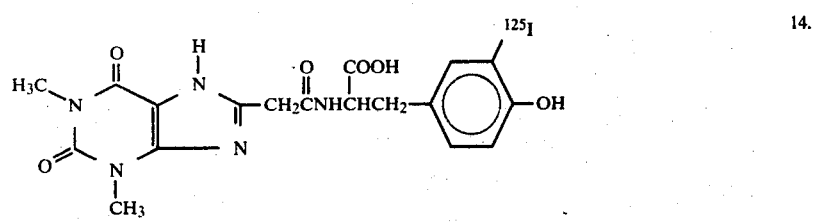 14.
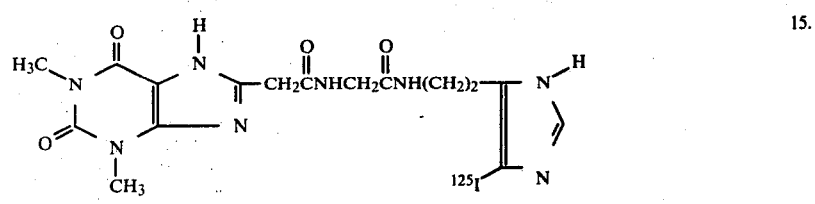 15.
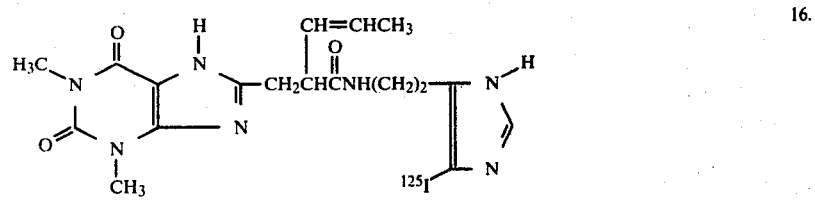 16.
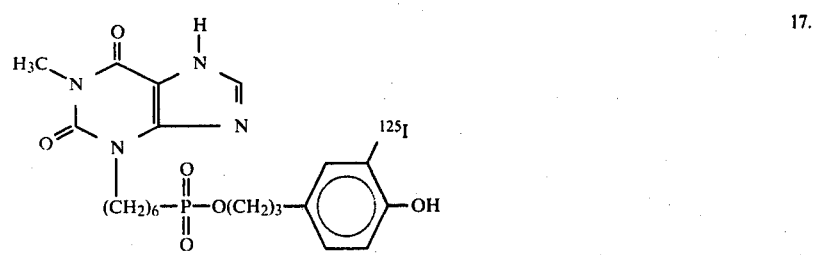 17.
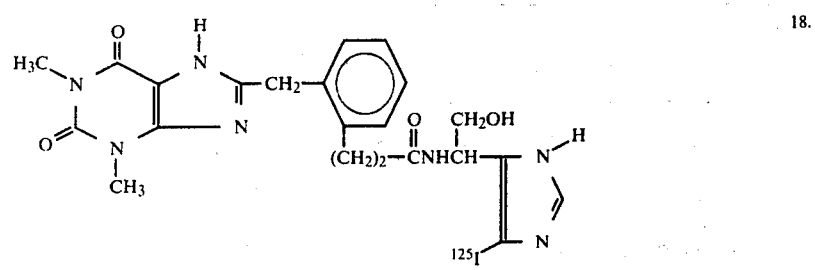 18.

TABLE-continued
Xanthine Tracers
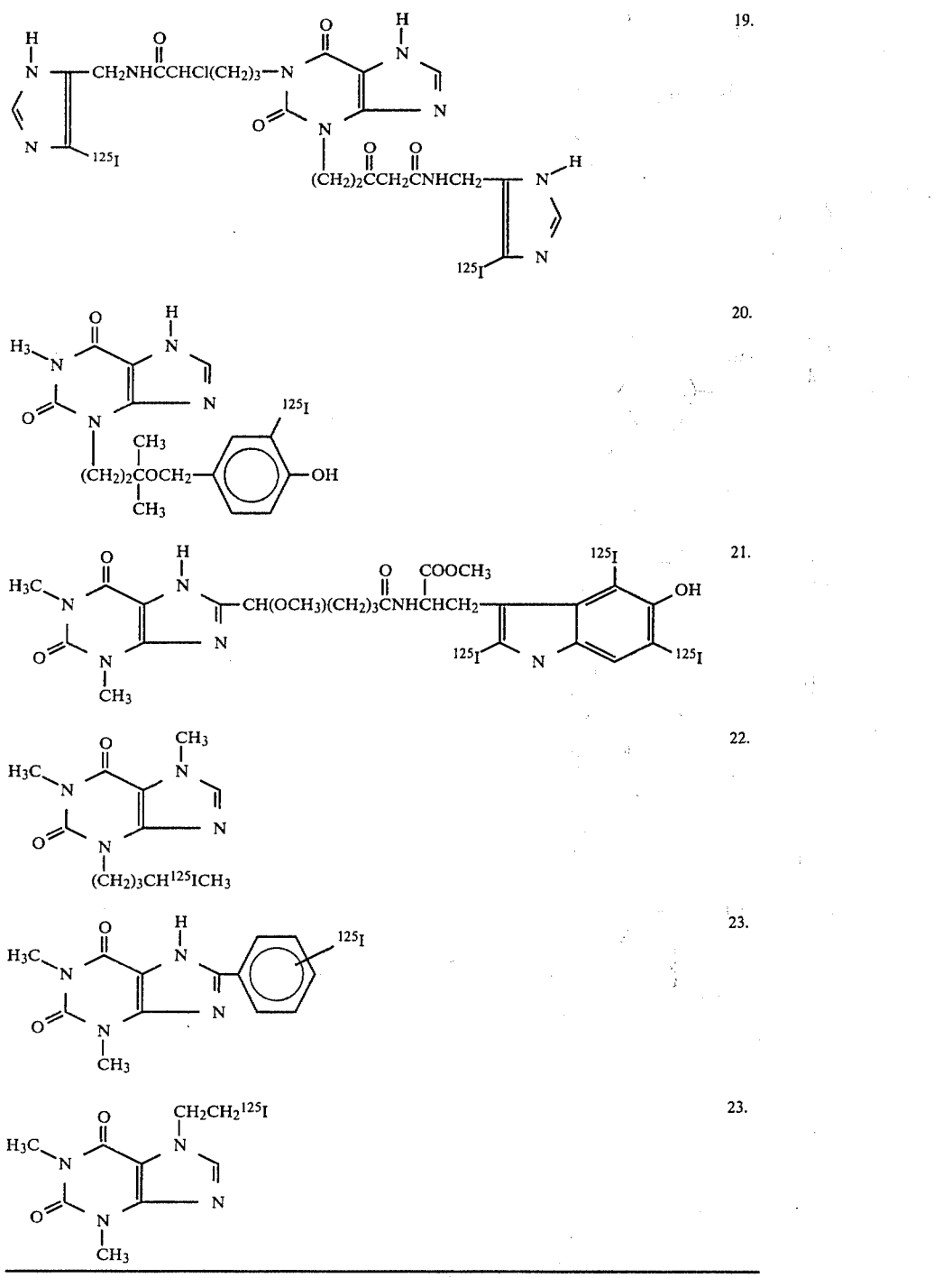
Representative tracers of this invention for radioimmunoassay of xanthine derivatives may be prepared by
(a) providing a starting compound having the structure
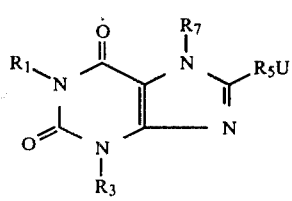

wherein
(i) $R_5$ is a bond; a cyclic, normal or branched chain alkylene or alkenylene; or such alkylene or alkenylene substituted with halo, hydroxy, keto, alkoxy, alkoxycarbonyl, carboxyl, amino or alkylamino groups;
(ii) U is carboxyl or amino; and
(iii) $R_1$, $R_3$ and $R_7$ are identical to the substituents at these positions in the xanthine derivative to be radioimmunoassayed;

(b) providing a radioiodinatable or radioiodinated compound having a carboxyl substituent if U is amino or an amino substituent if U is carboxyl;

(c) forming a mixed anhydride by reacting the carboxyl substituent with an activating agent; and (d) reacting the mixed anhydride with the amino substituent to form a peptide bond between the radioiodinatable or radioiodinated compound and the starting compound.

The starting compound described above may be prepared by synthesizing 8-(carboxyalkyl)-1,3-dimethylxanthine following the method of Cook et al, "Research Communications in Chemical Pathology and Pharmacology" 13(3):497–505 (1976). The carboxyalkyl moiety of this compound may be supplied with the various $R_5$ substituents discussed above by employing a cyclic anhydride containing those substituents. The length of the anhydride carbon chain will be proportional to the length of the carboxyalkyl moiety.

The carboxyl derivative is then coupled to an amino-substituted radioiodinatable ring-containing compound, an amino-substituted radioiodinatable aliphatic group or an amino-substituted preradioiodinated compound by generation of mixed anhydride using an activating agent such as ethyl chloroformate, isobutyl chlorformate of pivaloyl chloride in a conventional anhydrous aprotic solvent at low temperature (0°–10° C.). N,N-dimethyl formamide is the preferred solvent and one equivalent of organic base such as triethylamine is added to consume hydrochloric acid generated in the mixed anhydride formation. The amino compound to be coupled to the mixed anhydride is added to the reaction mixture in either aqueous solution or a mixed organic solvent; the reaction of the amino compound with the anhydride is apparently more rapid than hydrolysis of the anhydride.

Isolation of the desired compound may be accomplished by chromatography on an anion exchange resin, which is preferable, or by other known techniques such as thin layer chromatography on silica gel.

The tracers of this invention in which the xanthine 1, 3, or 7 positions are substituted with radioiodinated or radioiodinatable radicals, i.e. which are N-substituted, may be prepared by first forming an alkali metal, e.g., potassium or sodium, salt of the xanthine derivative to which the assay is to be directed. This salt is then reacted with a lower alkyl ester of an ω-halogenated normal or branched chain alkyl acid ester having the structure designated

where X is halogen such as bromine, $R_5$ is defined above with the exception that $R_5$ may not be a bond, and B is lower alkyl of from 1 to about 7 carbon atoms, preferably ethyl or methyl. This reaction produces a mixture of N-carboxyl esters which may be separated optionally by conventional means such as thin layer chromatography or chromatography on an anion exchange resin and the desired substituted xanthine recovered. The carboxyl ester is then hydrolyzed to produce the free acid. The acid may then be condensed with amino-substituted radioiodinated or radioiodinatable compounds such as the radioiodinatable ring-containing compounds, radioiodinatable aliphatic groups or preradioiodinated compounds described above.

Where a radioiodinatable compound has been produced in any of the foregoing methods, as opposed to a finished tracer, the radioiodinatable compound may be substituted with $^{125}I$ or $^{131}I$ in accordance with any of the following methods:

(1) Chloramine T Method of Hunter-Greenwood, W. Hunter, R. C. Greenwood, "Nature", 194:495 (1962);

(2) Iodine Monochloride Method, M. Ceska, F. Grossmuller, U. Lundkvist, "Acta Endocrinologia" 64:111–125 (1970);

(3) Isotopic Exchange Method, R. E. Counsell, V. V. Ranade, P. Pocha, R. E. Willette, W. Diguilio, "J. Pharmaceut, Sciences" 57:1657 (1968);

(4) Electrolytic Iodination, R. Pennisi, U. Rosa, "J. Nuclear Biol. and Medicine" 13:64 (1964); and (5) Enzymatic Iodination, H. Van Vanakis, J. J. Langone, L. J. Riceberg, L. Levine, "Cancer Research" 34:2546–2552 (1974).

The water soluble products of this invention may be iodinated in inert solvents such as water or water-alcohol mixtures.

Separation of unreacted radioactive iodine is accomplished by ion exchange chromatography and the use of aqueous solvents that selectively elute unreacted inorganic iodide and the desired iodinated product.

The preferred radioimmunoassay technique for use with the tracers of this invention is a competitive binding assay which utilizes a precipitating antiserum reagent to separate antibody-bound tracer from unbound tracer.

The procedure is based on the well-known competitive binding radioimmunoassay. In the case of theophylline, non-radioactive theophylline, whether from serum samples, theophylline standards, or controls, competes with a constant amount of $^{125}I$ theophylline tracer for binding sites on the theophylline antibody, which is held at a limiting concentration. The amount of $^{125}I$ theophylline tracer which will bind to the antibody is inversely proportional to the amount of non-radioactive theophylline present in the assay tube.

A precipitating reagent solution containing an antibody to antitheophylline is used to immunoprecipitate the antibody-bound $^{125}I$ theophylline, thus separating bound and unbound tracer. The assay tubes are then centrifuged and the supernatants are decanted. The double antibody-bound $^{125}I$ theophylline, which is located in the centrifugal pellet, is counted in a well-type, solid crystal gamma counter. A standard curve is constructed and the theophylline concentrations of the samples are interpolated from the standard curve.

The invention will be more fully understood in view of the following examples.

EXAMPLE 1

A. Synthesis of Theophylline-8-(4-Butyric Acid)

A mixture of 2.0 g of 4,5-diamino-1,3-dimethyl pyrimidine-2,6-dione and 2.68 g of glutaric anhydride in 150 ml of N,N-dimethyl formamide (N,N-DMF) is refluxed for 3 hours under a nitrogen purged Dean-Stark apparatus. The yellow crystals obtained are washed with 300 ml of benzene. Recrystallization is effected by dissolution in boiling water, filtration, cooling and isolation of the yellow-white crystals:

Approximate yield 40%; m.p. 143144° C.; main IR peaks 3190, 1760, 1650, 1505, 1415 cm$^{-1}$; $\lambda_{max}^{MeOH}$ 209, 275; elemental analysis:

$C_{11}H_{14}N_4O_4$

Calculated: C 49.62, H 5.30, N 21.04 Found C 49.55, H 5.50, N 20.99

B. Synthesis of Theophylline-8-(4-Butyryl-N-Histamine)

100 mg of theophylline-8-(4-butyric acid) is placed in a 12×75 mm glass test tube and dissolved in 4 ml of N,N-DMF. After chilling on an ice-water bath, 52.5 μl of triethyl amine is added and swirled. This is followed by addition of 44.2 μl of isobutyl chloroformate. The reaction proceeds for 30 minutes. Histamine free base, 46.0 mg, is dissolved in 4 ml of water and is added to the activated theophylline-8-(4-butyric acid) and left at 4° C. for 16 hours.

The aqueous layer is applied to an Amberlite XAD-2 gel permeation column, washed with water, and eluted with ethanol which is subsequently concentrated and lyophilized to yield about 10 mg of yellow solid. TLC in 100% ethanol shows a single spot that stains for histamine (Pauly stain).

EXAMPLE 2

Iodination of theophylline-8-(4-butyryl-N-histamine) is effected by the method of Hunter and Greenwood. 10 μl of a solution of 0.75 mg of the compound of Example 1 in 3.38 mls of a 0.5 M phosphate buffer pH 8.0 is placed into a 12×75 mm glass tube. To this is added 0.5 mCi of sodium iodide $^{125}$I in 5 μl of 0.1 N NaOH followed by 10 μl of an aqueous solution of chloramine-T (50 mg in 10 mls of distilled water). After reaction at room temperature for three minutes with occasional swirling, the reaction is quenched by the addition of 10 μl of a solution of sodium metabisulfite (300 mg in 10 ml of distilled water). The desired product, theophylline-8-(4-butyryl-N-[4-$^{125}$I] histamine), is recovered and separated from unreacted iodide by chromatography on an anion exchange column.

EXAMPLE 3

The tracer of Example 2 is used as the radiolabeled antigen in the competitive radioimmunoassay generally described above. 25 μl of patient serum is added to a duplicate pair of 12×75 mm polypropylene test tubes. Duplicate blank and standard tubes are prepared with 25 μl of 0 μg/ml, 15 μg/ml and 35 μg/ml theophylline solutions. 100 μl of tracer (2.5 μCi/15 ml) are added to each tube and the contents mixed gently, followed by 100 μl of rabbit anti-theophylline serum in phosphate buffered saline containing 0.02 M sodium azide and a polymeric precipitation aid. All tubes are then incubated for 15 minutes. 1.0 ml of goat anti-rabbit serum in isotonic phosphate buffer with 0.003 M sodium azide is added to each tube and the contents mixed by careful shaking. All tubes are immediately centrifuged for 10 minutes at a minimum relative centrifugal force of 850 xg in a refrigerated centrifuge at 4°–12° C. Each tube is then carefully decanted into a waste receptacle, followed by tapping each tube on an absorbent surface to remove any adhering supernatant. All tubes are then counted in a gamma counter with the window suitably adjusted for $^{125}$I.

The above examples and other specific information contained herein are for purposes of illustration only. Such alterations and modifications thereof as would be apparent to those skilled in the art are deemed to fall within the scope and spirit of the invention bearing in mind that the invention is defined only by the appended claims.

We claim:
1. The method of making a xanthene derivative which comprises
   (a) providing an alkali metal salt of a compound having the structure

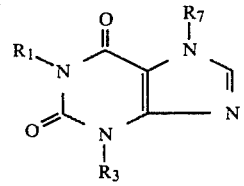

wherein at least one $R_1$, $R_3$ or $R_7$ is hydrogen, and, if not hydrogen, $R_1$ and $R_7$ are acetate or methyl and $R_3$ is methyl;
   (b) reacting the salt with a lower alkyl ester of an ω-halogenated normal or branched chain alkyl acid ester having the structure

wherein $R_5$ is hydrocarbon; X is halogen; and B is lower alkyl of from 1 to about 7 carbon atoms;
   (c) hydrolyzing the reaction product to form a free acid;
   (d) forming a mixed anhydride by reacting the free acid with an activating agent; and
   (e) condensing the mixed anhydride with an amino-substituted radioiodinated or radioiodinatable compound.
2. The method of claim 1 wherein $R_5$ is substituted with no more than two hydroxy, amino or alkoxy substituents.
3. The method of claim 1 wherein the amino-substituted radioiodinatable compound is tyrosine, tyrosinol, 4-(2-aminoethyl)phenol, histidine, histidinol, histamine, and polypeptides containing tyrosine or histidine.
4. The method of claim 1 including the additional step of radioiodinating the xanthine derivative.
5. The method of making a xanthine derivative which comprises
   (a) providing a starting compound having the structure

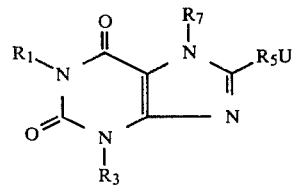

wherein (i) $R_5$ is a bond; a cyclic, normal or branched chain alkylene or alkenylene; or such alkylene or alkenylene substituted with halo, hydroxy, keto, alkoxy, alkoxycarbonyl, carboxyl, amino or alkylamino groups;
(ii) U is carboxyl or amino; and
(iii) $R_1$, $R_3$ and $R_7$ are identical to the substituents at these positions in the xanthine derivative to be radioimmunoassayed;

(b) Providing a radioiodinatable or radioiodinated compound having a carboxyl substituent if U is amino or an amino substituent if U is carboxyl;

(c) forming a mixed anhydride by reacting the carboxyl substituent with an activating agent; and (d) condensing the mixed anhydride with the amino substituent to form a peptide bond between the radioiodinatable or radioiodinated compound and the starting compound.

6. The method of claim 5 wherein $R_5$ contains no more than two hydroxy, amino or alkoxy substituents.

7. The method of claim 5 wherein the amino-substituted radioiodinatable compound is tyramine, tyrosine, tyrosinol, 4-(2-aminoethyl) phenol, histidine, histidinol, histamine, and polypeptides containing tyrosine or histidine.

8. The method of claim 5 including the additional step of radioiodinating the xanthine derivative.

* * * * *

UNITED STATES PATENT AND TRADEMARK OFFICE
CERTIFICATE OF CORRECTION

PATENT NO. : 4,397,779
DATED : Aug. 9, 1983
INVENTOR(S) : Ernest V. Groman, Michael D. Cabelli It is certified that error appears in the above-identified patent and that said Letters Patent are hereby corrected as shown below:

Column 4, line 49 change "infra" to -- _infra_ --.

Column 7, line 61, change "oridinarily" to -- ordinarily --.

Column 15, line 20, replace first "H₃ᐳN" to --H₃C─N --.

Column 17, line 33, please change "anhydride" to -- anhydrides --.

Column 17, line 51, please change "i.e." to -- "_i.e._" --

Column 17, line 52, please change "e.g." to -- _e.g._ --

Column 19, line 38, please change "NaOH" to -- _Na_OH --.

Column 20, line 29 after (b) add --forming N-carboxyl esters by--

Signed and Sealed this

Twenty-eighth Day of February 1984

[SEAL]

Attest:

GERALD J. MOSSINGHOFF

*Attesting Officer*  *Commissioner of Patents and Trademarks*